United States Patent [19]

Buxton et al.

[11] Patent Number: 4,885,249

[45] Date of Patent: Dec. 5, 1989

[54] ASPERGILLUS NIGER TRANSFORMATION SYSTEM

[75] Inventors: Franics P. Buxton, Toronto; David I. Gwynne, Brampton; Roger W. Davies, Limehouse, all of Canada

[73] Assignee: Allelix, Inc., Mississauga, Canada

[21] Appl. No.: 678,578

[22] Filed: Dec. 5, 1984

[51] Int. Cl.⁴ .................. C12N 15/00; C12N 1/14; C12P 21/00

[52] U.S. Cl. ...................... 435/172.3; 435/69.1; 435/172.1; 435/254; 435/320; 935/55; 935/56; 935/68

[58] Field of Search .................. 435/68, 70, 71, 91, 435/172.3, 254, 317, 172.1, 320; 536/27; 935/24, 14, 55, 56, 68

[56] References Cited

U.S. PATENT DOCUMENTS

| | | | |
|---|---|---|---|
| 4,486,533 | 12/1984 | Lambowitz | 435/91 |
| 4,735,901 | 4/1988 | Kurtz et al. | 435/172.3 |

FOREIGN PATENT DOCUMENTS

| | | |
|---|---|---|
| 0191221 | 8/1986 | European Pat. Off. |
| 0215594 | 3/1987 | European Pat. Off. |
| 0225078 | 10/1987 | European Pat. Off. |
| WO87/04464 | 7/1987 | World Int. Prop. O. |

OTHER PUBLICATIONS

Ballance et al., "Transformation of *Aspergillus nidulans* by the Orotidine-5'-phosphate Decarboxylase Gene of *Neurospora crassa*", Biochem. Biophys. Res. Comm. 112: 284 (1983).

Tilburn et al., "Transformation by Integration in *Aspergillus nidulans*", Gene 26; 205 (1983).

Berse et al., "Cloning and Characteristics of the Ornithin Carbamoyltransferase Gene from *Aspergillus nidulans*", Gene 25: 109 (1983).

J. W. Bennett, "Molds, Manufacturing & Molecular Genetics", Molecular Genetics of Filamentous Fungi, 1985, pp. 345-366.

D. J. Ballance, "Sequences Important for Gene Expression . . . " Yeast, vol. 2, 1986, pp. 229-236.

R. C. Ullrich et al., "Transforming Basidiomycetes", Molecular Genetics of Filamentous Fungi, 1985, pp. 39-57.

G. Turner et al., "Cloning & Transformation in *Aspergillus*", Gene Manipulations in Fungi, 1985, pp. 259-278.

F. P. Buxton et al., "Transformation of *Aspergillus niger* Using . . . ", Gene, 1985, pp. 207-214.

J. W. Bennett, "Prospects for a Molecular Mycology", Gene Manipulations in Fungi, 1985, pp. 515-527.

J. M. Kelly et al., "Transformation of *Aspergillus niger* ny the amdS Gene of . . . ", The EMBO Journal, vol. 4, No. 2, 1985, pp. 475-479.

M. E. Case et al., "Efficient Transformation of *Neurospora crassa* . . . ", Proc. Natl. Acad. Sci. U.S.A., vol. 76, No. 10, Oct. 1979, Genetics, pp. 5259-5263.

F. P. Buxton et al., "The Transformation of Mycelial Spheroplasts of Neurospora . . . ", Mol Gen Genet, 1984, 196:339-344.

Punt, P. J. et al., "Transformation of Aspergillus Based on the Hygromycin B Resistance Marker from *Escherichia coli*", Gene 56(1987), 117-124.

Ward, M. et al., "The oliC3 Gene of *Aspergillus niger* . . . ", Current Genetics, (1988)14, pp. 37-42.

Hartingsveldt, W. van et al., "Development of a Homologous Transformation . . . ", Mol Gen Genet (1987)206:71-75.

*Primary Examiner*—James Martinell
*Attorney, Agent, or Firm*—Nixon & Vanderhye

[57] ABSTRACT

Transformants of *Aspergillus niger* and related Aspergilli, containing foreign DNA conferring modified properties of expression thereon, are prepared by use of a DNA vector which contains a selectable marker which is capable of incorporation into the DNA of the host *A. niger* cells, but which is not to be found in the *A. niger* cells prior to this transformation. The vector also contains other foreign DNA to be incorporated into the *A. niger*, for modified expression. The process suitably uses mutants of *A. niger* as hosts, the mutants lacking the selectable marker as compared with wild type *A. niger*, and conducts the transformation on spheroplasts of *A. niger*.

22 Claims, 2 Drawing Sheets

ASPERGILLUS NIGER TRANSFORMATION SYSTEM

FIELD OF THE INVENTION

This invention relates to fungal transformants, and to methods of effecting transformation of fungi. More specifically, it relates to transformation of the filamentous fungal species *Aspergillus niger* and related *Aspergilli*, intermediates for use therein, and novel, useful fungal transformants thereof produced by genetic engineering techniques.

BACKGROUND OF THE INVENTION

The fungal species *Aspergillus niger* is used widely in the industrial production of enzymes, e.g. for use in the food industry. Its use is based on the secretory capacity of the microorganism. *A. niger* is used in large quantities and on a commercial scale for this industrial production, and is consequently a well-characterized microorganism. To apply genetic engineering techniques to *A. niger*, it is necessary to transfer DNA into *A. niger* so that the resultant fungal transformant may express an additional useful product and secrete it in large amounts.

Numerous genes have been cloned in a variety of prokaryotic vectors, and efforts are being made to obtain high expression levels for the encoded proteins. Genes are likely to be more efficiently expressed and processed and to produce a product more nearly the same as the original protein if these genes are placed into a host that is the same as or closely related to the species from which the gene was originally extracted.

However, very high levels of expression of individual proteins can be deleterious, if not lethal, to the cell if allowed to build up to high concentrations therein, and can cause crystallization of the protein into inactive and highly insoluble inclusion bodies. Thus one should develop systems that allow efficient excretion of synthesized proteins from the cell. Also, it is best to chose as hosts organisms which have been grown commercially, so that the already well developed fermentation technology and downstream processing can be exploited in the production of novel products or the increased production of existing products. *A. niger* is the source organism for numerous industrially important proteins, enzymes and other products. It is also capable of excreting highly expressed proteins. The transformation of filamentous fungi such as *A. niger* has however proved particularly difficult.

BRIEF REFERENCE TO THE PRIOR ART

European Patent Application No. 83303903.5 Lambowitz (assigned to St. Louis University), published Jan. 25, 1984, discloses functional extrachromosomal elements capable of replication in filamentous fungi, particularly of the class Ascomycetes, which includes the genera Neurospora, Aspergillus and Penicillium. In the process disclosed in this patent application, mitochondrial plasmid DNA is isolated from an Ascomycetes strain, linearized or further restricted, and cloned in an appropriate vector, such as a vector from *E. Coli* e.g. pBR322. The shuttle vector construct so formed contains the filamentous fungal mitochondrial replication system and prokaryotic replication systems. The construct is used to transform a filamentous fungal host. The foreign DNA is introduced into the host in this way as plasmid DNA, and is not apparently incorporated into the nuclear DNA. The reported experimental work however only uses *Neurospora crassa* as host organism.

Preparation of spheroplasts from filamentous fungi and the transformation thereof with DNA, containing a selectable marker in the filamentous fungi in a prokaryotic replicon, have been described for: *Neurospora crassa* by Case et al Proc. Natl. Acad. Sci. U.S.A. (1979) 76, 5259–5263 and Buxton et al, Molecular General Genetics (1984) 196, 339–344; and *Aspergillus nidulans* by Ballance et al Bioch. Bioph. Res. Commun. (1983) 112, 284–289, Tilburn et al Gene (1983) 26, 205–221. The cloning and characterization of arg B+ of *A. nidulans* is described by Berse et al Gene (1983) 25, 109–117.

SUMMARY OF THE INVENTION

It is an object of the present invention to provide a novel process for transforming a filamentous fungi of the species *Aspergillus niger* or related *Apergilli* with exogenous DNA.

It is a further object to provide novel and useful transformants of *Aspergillus niger*.

It is a further object to provide *A. niger* transformants containing re-introduced engineered genes of *A. niger* or other foreign DNA, in the species *A. niger*, and in which such foreign DNA is contained in the nuclear DNA.

In accordance with the present invention, transformants of the fungal species *Aspergillus niger* (or related *Aspergilli*) are prepared, which contain foreign DNA conferring modified properties of expression on the *Aspergillus niger*, and having a rapidly selectable phenotype permitting them to be readily differentiated from the original *Aspergillus niger*.

In the process of the present invention, *Aspergillus niger* is transformed by use of a DNA vector which contains a selectable marker which is capable of incorporation into the DNA of the host *A. niger* cells, but which is not to be found in the *A. niger* cells prior to this transformation. The vector may also contain other foreign DNA sequences required to be introduced into the *A. niger*, to enhance or modify its useful expressions of proteins. Then the transformants so formed can be selected and isolated from the unchanged cells on the basis of the selectable marker incorporated therein, grown and cultivated in the usual way, to provide colonies of transformants of *A. niger* with enhanced or modified capabilities of useful protein expression.

BRIEF REFERENCE TO THE DRAWINGS

FIG. 1 of the accompanying drawings is a diagrammatic representation of the process for preparing vector plasmid pDG1 for use in preparing *A. niger* transformants in accordance with the present invention;

FIG. 2 is a similar diagrammatic representation for preparing alternative vector plasmid pDG3.

DESCRIPTION OF THE PREFERRED EMBODIMENTS

Figure 1:
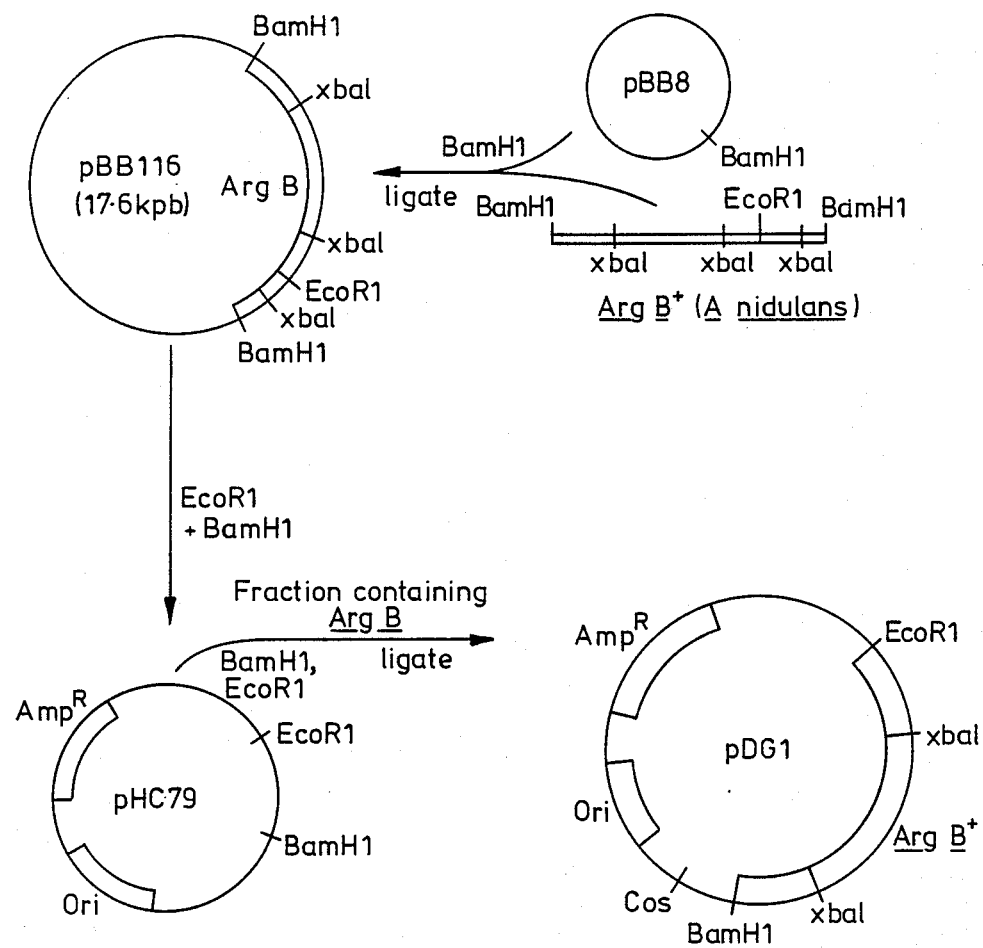

The selectable marker used in the present invention is suitably one which is naturally present in *A. niger*, so that its presence in the transformants will not materially affect the properties thereof as compared with the wild type *A. niger*. Thus, in the preferred process of the invention, a mutant strain of *A. niger* is used as the host for transformation, the mutant being one which lacks the chosen genetic marker as compared with the wild type *A. niger*. The mutant is transformed with a vector containing the selectable marker and the foreign DNA required to be incorporated, to modify or enhance the properties of expression of *A. niger*.

The use of a mutant *A. niger* strain to be transformed, coupled with a vector plasmid capable of complementing the *A. niger* mutant host, allows for straightforward selection and isolation of successfully transformed cells from unchanged host cells. It enables one to avoid reliance for selection on the other foreign DNA introduced by the vector plasmid which, although perhaps containing the gene which it is primarily desired to incorporate for its properties of expression in *A. niger*, may not provide the basis of easy and rapid selection and separation of the transformants.

In occasional cases, where the desired modification to *A. niger* is to introduce DNA sequences which will express a specific protein not normally present in *A. niger*, and which has an easy assay, these sequences themselves might constitute a dominant selectable marker, and hence permit the use of wild type *A. niger* as host. However, such instances are rare.

In specific applications, it may be necessary to avoid having to obtain a mutant in the desired host. To transform a wild type *A. niger*, one can use a dominant selectable marker, i.e. a gene which specifies a novel phenotype such as ability to utilise a metabolite that is not usually metabolized by *A. niger*, or ability to resist toxic effects of a chemical or antibiotic. Transformants of the wild type *A. niger* can then be selected on the basis of the dominant selectable marker introduced therein.

A specific preferred example of a selectable marker is the Arg B+ gene coding for the enzyme ornithine transcarbamylase. This enzyme is present in wild type *A. niger*. Mutants lacking this enzyme (Arg B− strains) can be prepared by usual non-specific techniques, e.g. treatment with ultraviolet radiation, and selected by their ability to grow on a medium containing arginine, but not on minimal medium. Transformants made according to the process of the invention, from an Arg B− strain of *A. niger* and a vector containing the Arg B+ gene, are consequently Arg B+ and are readily selectable and isolatable from the non-transformed Arg B− strain, by standard plating out and cultivation techniques.

While it is preferred, as described above, to utilize a selectable marker which is natural to wild type *A. niger*, it is not in fact essential that the selectable marker as used in the vector be actually derived from *A. niger*. It can equally well be obtained from another, similar species which also contains the required gene, subject to limitations of expression. Thus, in the preferred case under the present invention, the selectable marker Arg B+ can be obtained by treatment of fungal DNA of species *Aspergillus nidulans* with appropriate restriction enzymes, and then ligated into a suitable vector plasmid for use in transforming *A. niger* (Arg B−).

In the preferred embodiment of the process of the present invention, spheroplasts of *A. niger* are prepared and used in the transformation. The preferred method of preparing the spheroplasts is by enzymatic digestion of the cell walls, using for example cellulases. The selection of a suitable enzyme for enzymatic digestion of *A. niger* to produce spheroplasts thereof is within the skill of the art, perhaps requiring some routine screening tests. Useful enzymes are those capable of digesting complex polysaccharides, and are found among those known as effective in preparing fungal spheroplasts of a wide variety of fungal species. Specific examples of suitable enzymes include Novozym 234 (an impure mutanase) and B-glucuronidase. Other suitable methods may be used to form spheroplasts. Moreover, with suitable methods for cell wall penetration by the vectors, whole cells of *A. niger* may be used, instead of spheroplasts.

Transformations according to the present invention are suitably conducted using an appropriately chosen vector plasmid. To be suitable for use herein, the vector must contain the chosen selectable marker (e.g. Arg B+), and it must contain the other useful gene which the transformants are to contain. The vector may comprise linear or circular DNA. Preferably the vector also contains an *E. coli* replicon so that it can be manipulated and replicated therein, for introduction of selectable markers and the like, and preparation of adequate quantities of the vector in *E. coli*.

In a specific embodiment, the present invention provides a transformation system that allows selection of arginine prototrophic colonies from an *Aspergillus niger* arginine auxotroph (arg B− 350(-)52) by treating spheroplasts, typically obtained by enzymatic (for example Novozym 234 and β-glucuronidase) digestion of the cell wall followed by subsequent purification, with DNA, in the form of a plasmid, that contains the ornithine transcarbamylase structural gene of *A. nidulans* in the presence of polyethylene glycol 4000 and $CaCl_2$. These transformants integrate the arg B+ piece of DNA into their chromosomes and are capable of expressing this gene. The transformants also take up the other DNA present in the plasmid, shown by the presence of sequences in the transformants that hybridize to pBR322 and Tn5 that are not present in the parental strain.

Thus, in summary, to perform the transformation described in this invention one needs a recipient strain and a piece of DNA of which a part is selectable in this strain, i.e. contains a selectable marker. The strain should be of the species *Aspergillus niger* or closely related species of the *Aspergillus* genera. However, the recipient strain and the transforming DNA have to be chosen so that the transformants obtained by the uptake of the DNA into the recipient have a readily selectable phenotype. Thus one can use recipients that are sensitive to toxic metabolites with a DNA that encodes resistance (e.g. G418 and Tn5) or recipients that are unable to grow on a particular source of carbon, nitrogen etc., with a DNA that encodes the ability to use this (e.g. acetamide and acetamidase), or use prototrophic recipients and a DNA that encodes the missing enzyme. *A. niger* strain 350(-)52 has been deposited under ATCC 20739, pDG1 under ATCC 53005 and pDG3 under ATCC 53006. The name and address of the depository is The American Type Culture Collection, 12301 Parklawn Drive, Rockville, Md. 20852, U.S.A.

The invention is illustrated in the following specific examples.

*Aspergillus niger* (ATCC 46951) was mutagenized with UV light and an isolate obtained that required ornithine or arginine for growth in a defined minimal media. This strain which lacks ornithine carbamoyl transferase was called arg B (350(-)52). Media for growing *Aspergillus niger* were as described for *A. nidulans* by Cove, Biochem Biophys Acta (1966) 113, 51–56. *Recombinant DNA*

Tn5 is described in Berg et al "Biotechnology" (1983) 1, 417–435; pHC79 is described in Hohn et al "Gene" (1980) 11, 291–296; pUC12 is described in Vieira et al "Gene" (1982) 19, 259-268; and pBB116 described in Berse et al "Gene" (1983) 25, 109-117.

Restriction enzymes were obtained from International Biotechnologies Incorporated and were used as per manufacturers instructions. Plasmids were prepared by the alkaline lysis procedures of Ish-Horowitz et al "Nucleic Acids Research" (1981) 9, 2989-2998.

The preparation and construction of two novel vector plasmids, useful in the process of the present invention, is diagrammatically illustrated in the accompanying drawings. In FIG. 1, the process utilizes the Arg B+ gene extracted by known techniques using the enzyme Bam H1 from DNA of A. nidulans. This fraction is initially ligated with known E. coli plasmid pBB8 using ligase to form plasmid pBB116, which is also known. Then plasmid pBB116 is treated with restriction enzymes EcoRI and Bam H1 to prepare fragments thereof. The fragment containing the Arg B+ gene may be isolated from the mixture by normal methods, e.g. agarose electrophoresis and electroelution, and purified. Then it is ligated with known E. coli plasmid pHC79 also cut with Bam H1 and EcoRI, to produce novel plasmid pDG1. If desired, isolation of the fragment may be omitted, the ligation step performed using the entire mixture, and the plasmids containing the desired sequences then selected by known methods. This novel plasmid contains the replication origin, Ori, derived from pHC79 permitting it to be produced in quantity by replication in E. coli. It contains the Arg B+ gene as a selectable marker in Aspergillus, and has other DNA sequences, which can be introduced by transformation by known techniques into spheroplasts of A. niger Arg B− mutants. The resulting transformants can be selected on the basis of their Arg B+ characteristic, from the non-transformed mutants, and isolated and cultivated.

Figure 2:
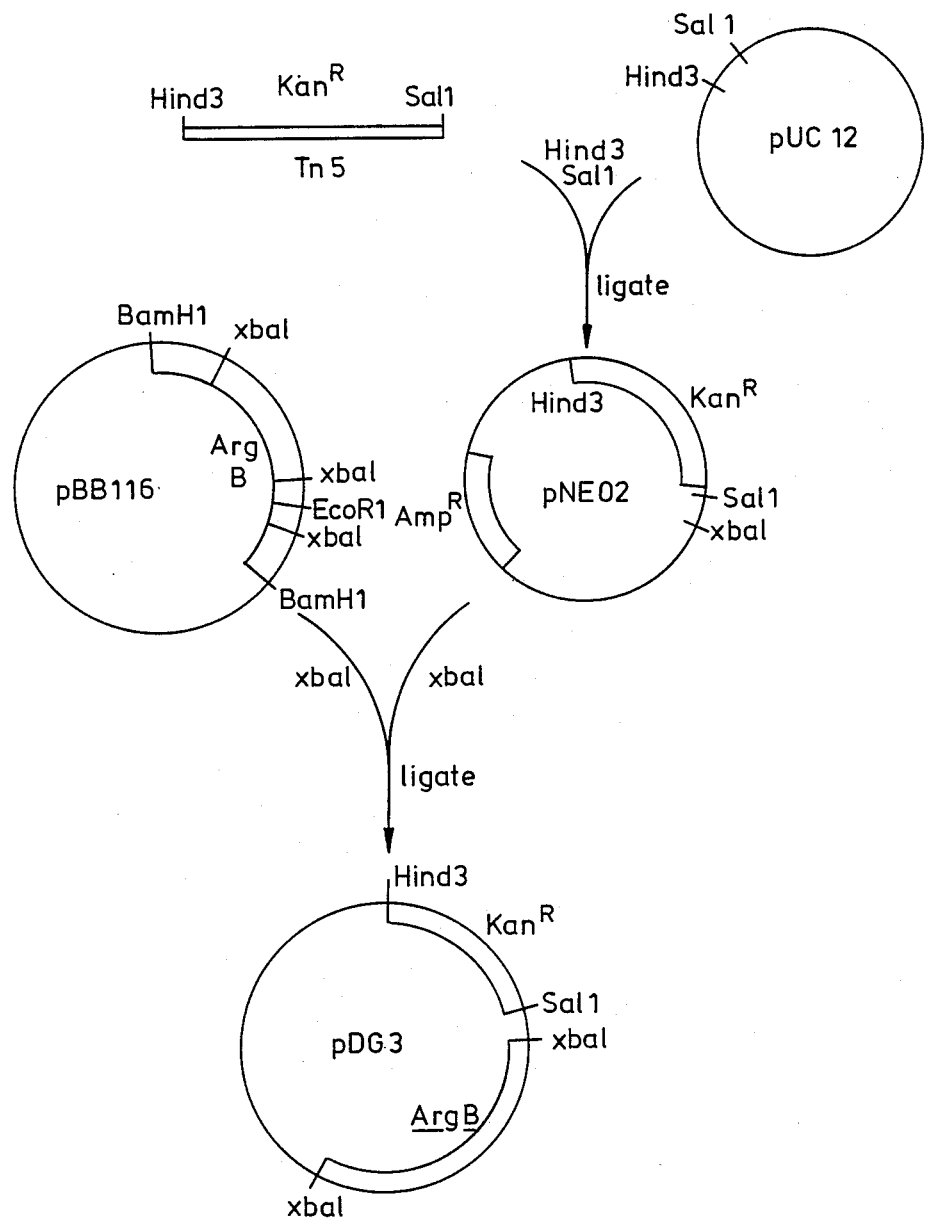

FIG. 2 diagrammatically illustrates a construction of alternative plasmid pDG3 for effecting transformation of A. niger strains Arg B−. In this process, known E. coli plasmid pUC 12 is ligated with a portion of the known transposon Tn5, specifically that portion containing the kanamycin resistance gene (Kan®), using restriction endonucleases Hind III and Sal I and T4 ligases. The resultant plasmid vector, pNE02, is then cut with XbaI and ligated with pBB116 XbaI fragments to produce plasmid pDG3. This novel plasmid pDG3 is approximately 7.4 kilo-base pairs long, and contains the Kan® gene derived from Tn5, the Amp® gene derived from pUC12 and the Arg B+ gene derived from pBB116. It can be used in transformations with spheroplasts of Arg B− mutants of A. niger.

Both pDG 1 and pDG 3 contain in their DNA sequences both the selectable marker Arg B+ and other DNA foreign to A. niger for incorporation into A. niger. This foreign DNA can include useful genes conferring novel and beneficial properties on A. niger transformants.

It is to be noted in connection with the present invention, that the vector comprising the foreign DNA is integrated into the genome of the recipient cell, i.e. it becomes part of the chromosomal or nuclear DNA, rather than remaining as a plasmid, so that the expression of the foreign DNA is thereafter permanent and there is little chance of its subsequent loss from the transformed cell. The novel phenotype of the transformants is thus very stable.

EXAMPLE 1

Transformation of Aspergillus niger 500 mls of complete media (Cove 1966)+0.02% arginine $+10^{-5}\%$ biotin in a 2 l conical flask was inoculated with $10^5$ conidia/ml of A. niger strain 350(-)52 (arg B) prepared as previously described, and incubated at 30° C., shaking at 250 rpm for 20 hours. The mycelia was harvested through Whatman No. 54 filter paper, washed with sterile deionized water and sucked dry. The mycelia was added to 50 ml of filter sterile 1.2 M MgSO$_4$ 10 mM potassium phosphate pH 5.8 in a 250 ml flask to which was added 20 mg of Novozym 234 (Novo Enzyme Industries), 0.1 ml (=15000 units) of β-glucuronidase (Sigma) and 3 mg of Bovine serum albumin for each gram of mycelia. Digestion was allowed to proceed at 37° C. with gentle shaking for 50-70 minutes checking periodically for spheroplast production by light-microscope. 50 mls of sterile deionised water was added and the spheroplasts were separated from undigested fragments by filtering through 30 μm nylon mesh and harvested by centrifuging at 2500 g for 5 minutes in a swing out rotor in 50 ml conical bottom tubes, at room temperature. The spheroplasts were washed, by resuspending and centrifuging, twice in 10 mls of 0.6 M KCl. The number of spheroplasts was determined using a hemocytometer and they were resuspended at a final concentration of $10^8$/ml in 1.2 M Sorbitol, 10 mM Tris/HCl, 10 mM CaCl$_2$ pH 7.5. 0.4 ml aliquots were placed in plastic tubes to which DNA either pDG 1 or pDG 3 in different experiments, (total vol. 40 μl in 10 mM Tris/HCl 1 mM EDTA pH 8) was added and incubated at room temperature for 25 minutes. 0.4 ml, 0.4 ml then 1.6 ml aliquots of 60% PEG4000, 10 mM Tris/HCl, 10 mM CaCl$_2$ pH 7.5 were added to each tube sequentially with gentle, but thorough mixing between each addition, followed by a further incubation at room temperature for 20 minutes. The transformed spheroplasts were then added to appropriately supplemented minimal media 1% agar overlays, plus or minus 0.6 M KCl at 45° C. and poured immediately onto the identical (but cold) media in plates. After 3-5 days at 37° C. the number of colonies growing was counted.

Transformants which have successfully taken up the Arg B+ and other DNA from the vector plasmids pDG 1 and pDG 3 will grow on minimal media plus KCl—the potassium chloride being necessary to prevent rupture of the spheroplasts. The results are given in the following Table.

| Type | DNA Added vol (μl) | wt (μg) | No. of transformants growing on minimal +KCl, after 6 days |
|---|---|---|---|
| none | 0 | 0 | 0 |
| pDG 1 | 40 | 20 | 12 |
| pDG 3 | 40 | 80 | 300 |

All viable cells and spheroplasts, including unchanged cells, unchanged spheroplasts, transformants, and revertants, will grow on minimal media plus arginine plus KCl. Such growth medium serves to check on the percentage survival of viable material, which was in these experiments in the range 40-90%. On minimal media plus arginine, only contaminating, non-spheroplast materials will grow. The contamination with such non-osmotically sensitive cells was less than 1% in the present experiments.

EXAMPLE 2

To check if these are genuine transformants rather than revertants, transformants were grown in minimal media, DNA was prepared from them, and they were probed with radioactively labelled plasmids.

Mycelia, grown from 36 to 72 hours from an inoculum of $10^5$ conidia/ml in 50 mls of appropriately supplemented media, were harvested through Whatman No. 54 paper and washed with distilled water. The mycelium was transferred to a cold mortar and ground to a fine powder in approximately 50 mls of liquid nitrogen with a pestle. This powder was poured into a 50 ml sterile siliconized conical flask to which was added 5 mls of 50 mM ethylenediaminetetraacetic acid, 0.2%, sodium dodecyl sulfate pH 8.5 and 5 µl of diethyl pyrocarbonate. This suspension was shaken for 1 minute at room temperature, then heated at 68° C. for 20 minutes. The cellular debris was removed by centrifuging the suspension in a 15 ml Corex tube at 4° C.×8000 rpm×15 minutes in a Sorvall SS34 rotor. Using wide mouthed Gilson tips 4 mls of the clear supernatant was removed to a fresh 15 ml Corex tube. To this was added 0.25 mls of 8 M acetic acid/KOH pH 4.2. This solution was incubated on ice for 45 minutes and the resulting precipitate was removed by centrifuging at 16000 rpm×15 min×4° C. in a Sorvall SS34 rotor. 3 mls of the clear supernatant was transferred as before to 3 mls of propan-2-ol in a fresh 15 ml Corex tube. After mixing, the DNA was pelleted by centrifuging at 10000 rpm×4 min×4° C. in a Sorvall SS34 rotor. The drained pellets were redissolved in 0.5 ml of 10 mM Tris/HCl 1 mM EDTA pH 7.5 by gentle agitation. This solution was transferred to 1.5 ml microfuge tubes and 1 µl of a 10 mg/ml stock of boiled RNAase was added. The RNA was digested at 37° C. for 20 minutes.

Then 60 µl of 3 M sodium acetate pH 6 and 660 µl of propan-2-ol was added. The precipitated DNA was pelleted by centrifuging at 15000 g for 2 mins. The pellet was dried briefly in a Speed-vac and then redissolved in 100 µl of 10 mM Tris/HCl 1 mM EDTA pH 8.

Southern transfers and hybridizations were as described in Buxton et al "Molecular General Genetics" (1983) 190:403–405. DNA for dot blots was denatured in 9 volumes of 1 M NaOH for 10 min and neutralized with a further 1.5 volume of 0.7 M Tris/HCl, 0.3 M NaCl, 20 mM EDTA, pH 6.8. After application to nitrocellulose using a Bethesda Research Laboratories's dot blot apparatus the filters were treated as for Southerns.

DNA from 8 transformants, A. niger strain 350(-)52 and A. nidulans FGSC4, were loaded onto dot-blots and probed with pBR322. Sequences homologous to pBR322 were detected in 6 of the 8 transformants, but not in either A. nidulans wild type or in the A. niger recipient from which these transformants were derived. A Southern blot was also done of BamHI digested DNA of these strains and probed with pDG1. A. nidulans wild type showed one BamHI fragment homologous to the arg B gene. Under the conditions of washing, A. niger 350(-)52 showed no bands hybridizing. Five of the transformants showed discrete bands, the same pattern not being observed in different transformants either indicating different integration events at the same locus or integration at different sites in the genome. Transformants obtained with pDG 3 also showed hybridization to Tn 5 sequences indicating the uptake of Kan ® gene from pDG 3.

Thus, it is concluded that A. niger (strain 350(-)52) arg B− has been transformed with the A. nidulans arg B+ gene. This gene is expressed in A. niger. The growth rates of transformants are not very good, so it is probably rather poorly expressed. The vector is also integrated into the genome along with the arg B+ gene 75% of the time in these transformants, so that a viable method of transforming foreign DNA into A. niger is provided.

EXAMPLE 3

The stability of the transformed phenotypes prepared as described above was checked. Transformants were inoculated from minimal media onto complete media and 10 mM arginine and grown for 5 days from a central inoculum. Conidia were removed from the edge of the colony diluted appropriately and plated onto minimal plus 10 mM arginine. After 3 days, colonies were replica plated onto minimal and minimal plus arginine. Out of 400 colonies tested from 8 transformants all were prototrophic indicating that the transformed phenotype is perfectly stable over this growth period as would be expected for any gene integrated into the genome.

We claim:

1. A process for transforming *Aspergillus niger*, said process comprising the steps of:
    treating an *Aspergillus niger* strain with recombinant DNA under conditions permitting at least some of said *Aspergillus niger* to take up said recombinant DNA and form transformants wherewith; and
    selecting resulting *Aspergillus niger* transformants.

2. The process of claim 1, wherein spheroplasts of said *Aspergillus niger* strain are treated with said recombinant DNA.

3. The process of claim 2, wherein said recombinant DNA is circular.

4. The process of claim 2, wherein said recombinant DNA is linear.

5. The process of claim 1, wherein said *Aspergillus niger* strain lacks a predetermined selectable marker and said recombinant DNA contains said predetermined selectable marker.

6. The process of claim 5, wherein said selectable marker is a gene of wild type *Aspergillus niger* and said strain of said *Aspergillus niger* which is treated with said recombinant DNA is a mutant strain thereof, deficient in said selectable marker.

7. The process of claim 6, wherein said selectable marker is able to confer antibiotic resistance to said transformants.

8. The process of claim 6, wherein said selectable marker is foreign to wild *Aspergillus niger*.

9. The process of claim 6, wherein said selectable marker is a gene which encodes an assayable product.

10. The process of claim 6, wherein said selectable marker is the ornithine carbamoyl transferase gene (Arg B+).

11. The process of claim 3 or 4, wherein said recombinant DNA comprises a replicon, permitting its replication in a bacterial host.

12. The process of claim 11, wherein said recombinant DNA comprises, as a selectable marker, ornithine carbamoyl transferase gene.

13. The process of claim 12, wherein said ornithine carbamoyl transferase gene is obtained from *Aspergillus nidulans*.

14. The process of claim 11, wherein said recombinant DNA is selected from the group consisting of pDG1 (ATCC 53005) and pDG3 (ATCC 53006).

15. A plasmid selected from the group consisting of pDG1 (ATCC 53005) and pDG3 (ATCC 53006).

16. Transformed *Aspergillus niger* comprising recombinant DNA.

17. *Aspergillus niger* ATCC 20739 transformed by *Aspergillus nidulans* argB gene.

18. A method for obtaining *Aspergillus niger* transformants, said method comprising the steps of:
enzymatically removing the cell wall of *Aspergillus niger*;
adding exogenous DNA to the resultant *Aspergillus niger* spheroplasts;
incubating the spheroplasts and exogenous DNA under conditions permitting some of the spheroplasts to take up exogenous DNA; and
isolating resulting *Aspergillus niger* transformants.

19. A method according to claim 18, wherein the exogenous DNA is linear.

20. A method according to claim 18, wherein the exogenous DNA is circular.

21. A method according to claim 18, wherein the exogenous DNA comprises the argB gene of *A. nidulans*.

22. A method according to claim 21, wherein the exogenous DNA comprising said argB gene is a plasmid selected from the group consisting of pDG1 (ATCC 53005) and pDG3 (ATCC 53006).

* * * * *